United States Patent
Ehler et al.

(10) Patent No.: US 9,877,760 B2
(45) Date of Patent: Jan. 30, 2018

(54) IMPLANT FOR PELVIC RING FRACTURES

(71) Applicant: Signus Medizintechnik GmbH, Alzenau (DE)

(72) Inventors: Sabrina Ehler, Hausen (DE); Alexander Harwart, Alzenau (DE); Frank Obermeier, Heppenheim (DE); Uwe Siedler, Alzenau (DE)

(73) Assignee: Signus Medizinetchnik GmbH, Alzenau (DE)

( * ) Notice: Subject to any disclaimer, the term of this patent is extended or adjusted under 35 U.S.C. 154(b) by 243 days.

(21) Appl. No.: 14/018,803

(22) Filed: Sep. 5, 2013

(65) Prior Publication Data
US 2014/0074175 A1 Mar. 13, 2014

Related U.S. Application Data

(60) Provisional application No. 61/706,236, filed on Sep. 27, 2012.

(30) Foreign Application Priority Data

Sep. 5, 2012 (DE) .................... 20 2012 103 384 U

(51) Int. Cl.
*A61B 17/84* (2006.01)
*A61B 17/70* (2006.01)
*A61B 17/86* (2006.01)
*A61B 17/80* (2006.01)

(52) U.S. Cl.
CPC ........ *A61B 17/846* (2013.01); *A61B 17/7055* (2013.01); *A61B 17/863* (2013.01); *A61B 17/7037* (2013.01); *A61B 17/8052* (2013.01)

(58) Field of Classification Search
CPC . A61B 17/70; A61B 17/7049; A61B 17/7055; A61B 17/72; A61B 17/7233; A61B 17/7241; A61B 17/725; A61B 17/84; A61B 17/844; A61B 17/846; A61B 17/86
See application file for complete search history.

(56) References Cited

U.S. PATENT DOCUMENTS

| | | |
|---|---|---|
| 4,418,422 A | 11/1983 | Richter et al. |
| 4,454,876 A | 6/1984 | Mears |
| 4,541,424 A | 9/1985 | Grosse et al. |
| 4,655,199 A * | 4/1987 | Steffee ............... A61B 17/7055 606/246 |
| 4,719,907 A | 1/1988 | Banko et al. |
| 4,917,111 A | 4/1990 | Pennig et al. |
| 5,108,397 A * | 4/1992 | White ................ A61B 17/8004 606/319 |
| 5,108,398 A | 4/1992 | McQueen et al. |

(Continued)

FOREIGN PATENT DOCUMENTS

| | | |
|---|---|---|
| AU | 2008201665 A1 | 5/2008 |
| CA | 2106887 A1 | 3/1995 |

(Continued)

*Primary Examiner* — Christian Sevilla
*Assistant Examiner* — Eric S Gibson
(74) *Attorney, Agent, or Firm* — Grossman Tucker Perreault & Pfleger, PLLC

(57) ABSTRACT

Implant for stabilization of pelvic ring fractures, comprising a nail for intraosseous implantation, a fixing agent and at least one locking element for relative fixation of the pelvic bone to the nail.

26 Claims, 6 Drawing Sheets

(56) References Cited

U.S. PATENT DOCUMENTS

Figure 1:
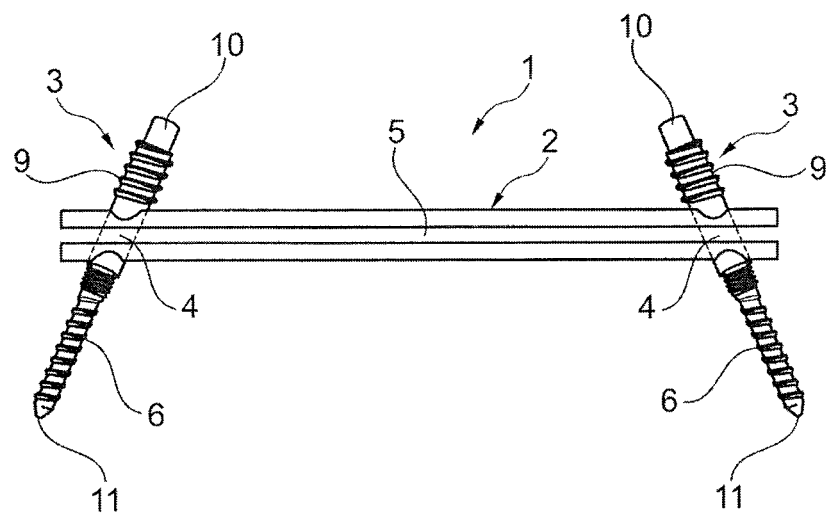

| | | | |
|---|---|---|---|
| 5,176,681 A * | 1/1993 | Lawes | A61B 17/921 606/64 |
| 5,334,192 A | 8/1994 | Behrens | |
| 5,382,248 A * | 1/1995 | Jacobson | A61B 17/686 606/267 |
| 5,472,444 A * | 12/1995 | Huebner | A61B 17/7283 606/62 |
| 5,478,343 A | 12/1995 | Ritter | |
| 5,480,402 A * | 1/1996 | Kim | A61B 17/1725 606/64 |
| 5,584,838 A | 12/1996 | Rona et al. | |
| 5,624,444 A | 4/1997 | Wixon et al. | |
| 5,769,856 A | 6/1998 | Dong et al. | |
| 5,788,700 A | 8/1998 | Morawa et al. | |
| 6,036,696 A | 3/2000 | Lambrecht et al. | |
| 6,039,739 A | 3/2000 | Simon | |
| 6,053,916 A | 4/2000 | Moore | |
| 6,090,113 A | 7/2000 | Le Couedic et al. | |
| 6,629,976 B1 * | 10/2003 | Gnos | A61B 17/7291 606/62 |
| 7,060,070 B1 | 6/2006 | Anastopoulos et al. | |
| 7,077,847 B2 | 7/2006 | Pusnik et al. | |
| 7,232,443 B2 | 6/2007 | Zander et al. | |
| 7,311,710 B2 | 12/2007 | Zander | |
| 7,549,994 B2 | 6/2009 | Zander et al. | |
| 7,686,818 B2 | 3/2010 | Simon et al. | |
| 7,722,611 B2 * | 5/2010 | Cavallazzi | A61B 17/1739 606/60 |
| 8,162,950 B2 | 4/2012 | Digeser et al. | |
| 2002/0055744 A1 | 5/2002 | Reiley | |
| 2002/0087161 A1 * | 7/2002 | Randall | A61B 17/683 606/916 |
| 2002/0133156 A1 * | 9/2002 | Cole | A61B 17/164 606/62 |
| 2002/0133172 A1 | 9/2002 | Lambrecht et al. | |
| 2002/0156473 A1 * | 10/2002 | Bramlet | A61B 17/744 606/62 |
| 2004/0092942 A1 | 5/2004 | Reiley | |
| 2005/0124995 A1 | 6/2005 | Reiley | |
| 2005/0125070 A1 | 6/2005 | Reiley | |
| 2005/0277936 A1 * | 12/2005 | Siravo | A61B 17/72 606/62 |
| 2006/0030852 A1 * | 2/2006 | Sevrain | A61B 17/68 606/328 |
| 2006/0036251 A1 | 2/2006 | Reiley | |
| 2006/0069392 A1 * | 3/2006 | Renzi Brivio | A61B 17/72 606/64 |
| 2006/0095040 A1 * | 5/2006 | Schlienger | A61B 17/686 606/64 |
| 2006/0155281 A1 * | 7/2006 | Kaup | A61B 17/7258 606/65 |
| 2006/0200160 A1 * | 9/2006 | Border | A61B 17/72 606/88 |
| 2007/0049940 A1 * | 3/2007 | Wallace | A61B 17/72 606/62 |
| 2007/0112432 A1 | 5/2007 | Reiley | |
| 2007/0123873 A1 * | 5/2007 | Czartoski | A61B 17/72 606/62 |
| 2007/0233100 A1 * | 10/2007 | Metzinger | A61B 17/7241 606/62 |
| 2007/0233101 A1 * | 10/2007 | Metzinger | A61B 17/72 606/62 |
| 2007/0233102 A1 * | 10/2007 | Metzinger | A61B 17/748 606/62 |
| 2007/0233103 A1 * | 10/2007 | Metzinger | A61B 17/72 606/62 |
| 2007/0233104 A1 * | 10/2007 | Metzinger | A61B 17/7241 606/62 |
| 2007/0299533 A1 | 12/2007 | Reiley | |
| 2008/0039857 A1 | 2/2008 | Giersch et al. | |
| 2008/0065227 A1 | 3/2008 | Reiley | |
| 2008/0132900 A1 | 6/2008 | Prien et al. | |
| 2008/0154306 A1 * | 6/2008 | Heinz | A61B 17/7055 606/256 |
| 2008/0183171 A1 * | 7/2008 | Elghazaly | A61B 17/744 606/64 |
| 2008/0249580 A1 * | 10/2008 | Evans | A61B 17/744 606/86 R |
| 2008/0269807 A1 | 10/2008 | Simon et al. | |
| 2008/0294164 A1 * | 11/2008 | Frank | A61B 17/7241 606/64 |
| 2009/0030418 A1 | 1/2009 | Volzow | |
| 2009/0099610 A1 | 4/2009 | Johnson et al. | |
| 2009/0105767 A1 | 4/2009 | Reiley | |
| 2009/0105840 A1 | 4/2009 | Reiley | |
| 2009/0131936 A1 * | 5/2009 | Tipirneni | A61B 17/683 606/64 |
| 2009/0131991 A1 * | 5/2009 | Tipirneni | A61B 17/683 606/301 |
| 2009/0177203 A1 | 7/2009 | Reiley | |
| 2009/0240338 A1 | 9/2009 | Reiley | |
| 2009/0259261 A1 * | 10/2009 | Reiley | A61B 17/8897 606/329 |
| 2009/0326533 A1 * | 12/2009 | Dell'Oca | A61B 17/725 606/64 |
| 2009/0326534 A1 * | 12/2009 | Yamazaki | A61B 17/7241 606/65 |
| 2010/0087878 A1 * | 4/2010 | Abdou | A61B 17/7055 606/86 R |
| 2010/0094290 A1 | 4/2010 | Vaidya | |
| 2010/0094293 A1 * | 4/2010 | McClellan | A61B 17/7241 606/64 |
| 2010/0241229 A1 * | 9/2010 | Baehre | A61B 17/00491 623/16.11 |
| 2010/0249781 A1 * | 9/2010 | Haidukewych | A61B 17/7241 606/62 |
| 2011/0066152 A1 * | 3/2011 | Keller | A61B 17/748 606/62 |
| 2011/0078887 A1 | 4/2011 | Bigdeli-Issazadeh et al. | |
| 2011/0184478 A1 | 7/2011 | Reiley | |
| 2011/0276099 A1 * | 11/2011 | Champagne | A61B 17/7225 606/328 |
| 2011/0282395 A1 * | 11/2011 | Beyar | A61B 17/1631 606/301 |
| 2011/0313420 A1 * | 12/2011 | LeCronier | A61B 17/7233 606/62 |
| 2012/0004734 A1 | 1/2012 | Reiley | |
| 2012/0010719 A1 | 1/2012 | Reiley | |
| 2012/0059428 A1 * | 3/2012 | Epperly | A61B 17/7225 606/310 |
| 2012/0089144 A1 | 4/2012 | Murner et al. | |
| 2012/0130433 A1 * | 5/2012 | Huebner | A61B 17/1686 606/300 |
| 2012/0143192 A1 * | 6/2012 | Watanabe | A61B 17/7225 606/64 |
| 2012/0197255 A1 * | 8/2012 | Elghazaly | A61B 17/725 606/64 |
| 2012/0226278 A1 * | 9/2012 | Nardini | A61B 17/7241 606/64 |
| 2013/0030436 A1 * | 1/2013 | LeCronier | A61B 17/725 606/64 |
| 2013/0041414 A1 * | 2/2013 | Epperly | A61B 17/7225 606/310 |
| 2013/0079829 A1 * | 3/2013 | Globerman | A61B 17/1728 606/286 |
| 2013/0090699 A1 * | 4/2013 | Holzwarth | A61B 17/1635 606/309 |
| 2013/0116693 A1 * | 5/2013 | Nelson | A61B 17/7233 606/64 |
| 2013/0211468 A1 * | 8/2013 | Huebner | A61B 17/863 606/328 |
| 2013/0238036 A1 * | 9/2013 | Sinha | A61B 17/68 606/304 |
| 2013/0325008 A1 * | 12/2013 | Kuxhaus | A61B 17/7233 606/63 |
| 2013/0325010 A1 * | 12/2013 | Prien | A61B 17/7216 606/64 |

(56) References Cited

U.S. PATENT DOCUMENTS

| | | | | |
|---|---|---|---|---|
| 2014/0058392 A1* | 2/2014 | Mueckter | ............. | A61B 17/744 606/64 |
| 2014/0074175 A1* | 3/2014 | Ehler | ................. | A61B 17/7055 606/329 |
| 2014/0094860 A1* | 4/2014 | Reimels | ............... | A61B 17/844 606/323 |
| 2014/0135850 A1* | 5/2014 | Parent | .................... | A61B 17/68 606/304 |

FOREIGN PATENT DOCUMENTS

| | | |
|---|---|---|
| CA | 2732970 A1 | 9/2011 |
| DE | 20217647 U1 | 1/2003 |
| EP | 0059044 A2 | 9/1982 |
| EP | 0167719 B1 | 4/1988 |
| EP | 0521600 A1 | 1/1993 |
| EP | 0809969 A2 | 12/1997 |
| EP | 0865766 A2 | 9/1998 |
| EP | 0903127 A2 | 3/1999 |
| EP | 0947169 A2 | 10/1999 |
| EP | 1661525 A2 | 5/2006 |
| EP | 1808138 A1 | 7/2007 |
| EP | 1842503 A1 | 10/2007 |
| EP | 1854611 A1 | 11/2007 |
| EP | 2229878 A1 | 9/2010 |
| WO | 8906948 A1 | 8/1989 |
| WO | 0130264 A2 | 5/2001 |
| WO | 02085182 A2 | 10/2002 |
| WO | 2006099270 A2 | 9/2006 |
| WO | 2008088685 A2 | 7/2008 |
| WO | 2009087214 A1 | 7/2009 |
| WO | 2010065015 A1 | 6/2010 |
| WO | 2011091349 A2 | 7/2011 |
| WO | 2012007054 A1 | 1/2012 |
| WO | 2012048008 A1 | 4/2012 |
| WO | 2012050572 A1 | 4/2012 |

* cited by examiner

IMPLANT FOR PELVIC RING FRACTURES

The invention relates to an implant for stabilizing pelvic ring fractures as well as degenerative changes and instabilities and arthroses in the iliosacral joint.

The pelvic ring comprises the sacrum (os sacrum or sacral bone) and two hipbones (ossa coxae), which laterally embrace the sacrum. A hipbone as the biggest bone comprises the ilium (os ilium or iliac bone) and also smaller bones such as the ischium (os ischii) and the pubic bone (os pubis). The ilium is connected to the sacrum through the iliosacral joint, which has a very low degree of mobility.

In the case of a pelvic ring fracture, which often is the consequence of a heavy fall or of traffic accidents, fractures may occur in the bones of the pelvic ring, for instance in the ilium or in the sacrum and also in the iliosacral joint. In former times, such fractures were not treated by surgery. Instead, the healing for achieving union of the fracture sites in the pelvic ring was promoted by mere immobilization. However, as this procedure frequently did not achieve satisfactory healing, various surgical techniques for the stabilization of pelvic ring fractures have established in recent times. Such stabilizations mainly focus on fixing bones to each other on both sides of the fracture so that the bones can grow together much better. At the same time it is intended to fix the bones in their original posture so that no permanent damage will remain after the fracture has healed. Surgical techniques for the stabilization of pelvic ring fractures normally use implants. Known implants are for instance bone screws used for screwing the bones against each other. The screws may comprise for instance a screw head and a bone-screw thread so that the bone-screw thread can be screwed through the bone and the screw head produces a surface pressure against two bone fragments along the fracture. Other known implants are screws that have a bone-screw thread on one end and a metric thread on the other end so that the screw is first screwed into a second bone fragment through a first bone fragment and a nut is then attached to the metric thread by which the surface pressure against the first bone fragment is created in a direction toward the second bone fragment. Additionally known are screws having a bone-screw thread with a first defined lead on one end and a bone-screw thread with a second defined lead on the second end, the second lead being larger or smaller than the first lead so that the surface pressure at the time of inserting the screws is created by the different feeding amount of the bone fragments. It is also known in the context of implants to use a different anchoring mechanism in a bone in place of a bone-screw thread. This can be achieved for instance by a wedge-shaped construction of an implant, wherein the implant is inserted headlong into the bone, mostly into a pre-drilled tunnel, and then clamped against the bone by exerting a force on the implant.

The known implants for stabilizing pelvic ring fractures allow bone fragments being pressed against each other, thus promoting the healing process. On the other hand, the known implants have the drawback that bone fragments cannot be fixed by these implants in an angular stable manner and particularly that no angular stable transsacral and/or transilial fixation can be produced. Angular stable fixation, i.e. fixation that prevents twisting of the bone fragments relative to each other at least partially, requires the provision of a plurality of such known implants. For example, the implants can be inserted into the bone fragments at different angles along the fracture plane between two bone fragments. On the other hand, this approach has the drawback that the bone fragments to be fixed together, particularly in the vicinity of the fracture, are degraded as a result of these many bores and/or screwed connections and/or clamping connections. A further disadvantage of the described implants is that the surface pressure between the bone fragments is created by the implant itself, whereby the contact positions between the implant and the bone are subject to load, which may lead to bone damage, especially at the interface between the implant and the bone which is particularly relevant to the bone's support.

Based on this prior art, it is an object of the present invention to provide an implant for stabilization of pelvic ring fractures solving at least partially the problems discussed in the context of conventional implants. In a similar manner, the invention is intended to be used where necessary also for carrying out an arthrodesis at degenerative instabilities and/or arthroses of the sacroiliac joint.

As a solution to the above-mentioned technical object the invention proposes an implant with the features of claim 1. The corresponding implant of the invention comprises a nail for intra-ossary implantation as well as at least one locking element for relative fixation of the pelvic bone with respect to the nail. The implant of the invention also comprises a fixing device. Here the term intra-ossary implantation is understood to mean an implantation inside a bone. Therefore, the nail of the inventive implant is constructed in such a manner that the nail can be intra-ossarily passed through the sacrum via a tunnel pre-drilled through a sacrum, or can be intra-ossarily inserted into the sacrum via a tunnel pre-drilled in the sacrum. Said nail has a transverse duct at least on one end thereof, for receiving the locking element. The locking element includes an anchoring section by which it can be anchored in a pelvic bone. The locking element also includes a locking section that corresponds with the transverse duct in such a manner that the locking element can be locked to the nail in an angular stable manner. On its second nail end, said nail can be fixed in a first pelvic bone and/or in the sacrum by means of said fixing device. Further, the nail can be securely fixed against twisting or displacement relative to a second pelvic bone by means of the locking element. Therefore, after the nail is fixed in a first pelvic bone and/or in the sacrum at its second nail end using said fixing device, the nail can be securely fixed against twisting or displacement relative to a second pelvic bone by means of the locking element.

Thus the nail can be initially fixed in a pelvic bone and/or sacrum at its second nail end using said fixing device and thereafter anchored in angular stable manner by means of the locking element.

The nail can be inserted for instance unilaterally. Here the nail can be inserted into the sacrum through a tunnel and fixed in the sacrum by means of the fixing device, for stabilizing a sacrum fracture for instance. Thereafter, angular stable anchorage in a pelvic bone such as an ilium can be effected, whereby the fracture in the sacrum is fixed as a result of said fixation of the sacrum with respect to said further pelvic bone. The fracture is then advantageously situated between the fixing point of the nail in the sacrum, which is determined by the co-action between the sacrum and the fixing device, and the fixing point of the nail in a pelvic bone, which is determined by the co-action of the locking element with the pelvic bone. Nevertheless, the nail can be inserted also bilaterally, for instance passed through a tunnel through the sacrum and fixed at both ends outside the sacrum at least in some areas, for instance in a respective ilium, namely first at its second end by means of the fixing device and thereafter at its first end by means of the locking element.

The anchoring section of the locking element is constructed in such a manner that it can be anchored in a pelvic bone. For example, said anchoring section can have the shape of a wedge and/or can comprise a bone-screw thread. The anchoring section can also have a surface that can easily grow together with a pelvic bone. The locking section of the locking element can be locked to the nail through the transverse duct of the nail. For example, the locking section can be constructed in such a manner that it may be fixed in the transverse duct of the nail by clamping. The surface of the locking section can for example include engagement hooks, or the locking section can be constructed in a wedge shape. A construction of the locking section in the manner of a split dowel is also possible. Further, the locking section can comprise a thread corresponding with a thread provided in the transverse duct of the nail. In this case, locking between the locking element and the nail can be established by screwing the locking element together with the nail. The locking section and the anchoring section of the locking element can be situated for instance directly adjacent to each other, can pass into each other seamlessly, or can also be spaced from each other.

The reception of the locking element in the nail can be effected by the locking element being first passed with its first end through the transverse duct of the nail. It may be advantageous for the locking element to be conically flattened on its first end. This facilitates insertion of the locking element into the transverse duct of the nail; in particular, in this case, the locking element can be inserted into the transverse duct without considerable problems, even if the locking element is tilted with respect to the extension direction of the transverse duct. The conical flattening of the locking element on its first end can be particularly advantageous in case the locking element is inserted into the transverse duct under the exertion of a considerable force.

Advantageously, a tool connector is provided on one end of the locking element. The tool connector can be constructed for example as a hexagon or any other type of screw head allowing easy screwing of the locking element. It also possible to provide for instance other coupling devices that can be coupled with a tool.

The nail which is used in the implant of the invention has a diameter such that the nail can be passed intra-ossarily through a tunnel pre-drilled through the sacrum and such that transverse ducts for receiving a locking element can be provided at the same time in the nail. Accordingly, the nail is required to have a certain minimum thickness, but the nail must not reach a thickness that would prevent the nail from passing through the sacrum because in this latter case there is a risk that the sacrum might be considerably impaired or that nerves might be touched which run along the sacrum.

Preferably, the nail in the implant of the invention can have such a length that the nail after being passed through the tunnel in the sacrum can be fixed in a first pelvic bone, particularly in a first ilium, at its second nail end by means of a fixing device and that after fixation the nail can be anchored in a second pelvic bone, particularly in the second ilium, at its first end by means of the locking element that can be anchored in the nail transverse duct. Accordingly, in this embodiment, the nail must be longer than the length of the tunnel through the sacrum. Here the length of the tunnel on the one hand depends on the individual width of the sacrum through which the nail must be passed, and on the other hand on the position where the tunnel is provided in the sacrum. The sacrum in the human body tapers top down and includes regions in which the sacrum is formed as a continuous bone throughout its width. These regions are described as S1, S2, S3, S4, or S5 corridor. Each of these regions corresponds to one vertebra, and the five vertebrae which form the respective corridor are fused in the sacrum. The S1 corridor is the corridor in the sacrum which is positioned the highest in the human body and where the sacrum has the largest width. The width of the sacrum decreases downwards, i.e. from corridor S1 towards corridor S5. For this reason, the nail must have a corresponding length, which depends on the corridor of the sacrum in which the tunnel is provided through which the nail of the inventive implant must be passed.

Preferably, in the implant of the invention, the nail may have such a length that after its insertion through the tunnel into the sacrum the nail can be fixed in the sacrum at its second nail end by means of a fixing device, and after fixation the nail can be anchored in a pelvic bone, particularly in an ilium, at its first end by means of the locking element that can be anchored in the nail transverse duct. In this embodiment, the nail is required to have such a length that after its insertion and fixation in the sacrum, the nail extends with its first end outside of the sacrum over a part of the ilium, but the length of the nail must be limited so that the nail cannot cause any damage outside of the pelvic ring.

Prior to fixation of the nail relative to a second pelvic bone by means of the locking element, the nail must be initially fixed at its second nail end in a first pelvic bone and/or in a sacrum by means of a fixing device. The fixing device can take different forms. In particular, the fixing device does not comprise a locking element, in one embodiment. For example, a thread can be provided on the second nail end as a fixing device, particularly in the manner of a bone-screw thread, so that the nail can be screwed into the first pelvic bone and/or into the sacrum. Also, the fixing device can be provided as a wedge-shaped construction of the nail so that the nail can be driven into the pelvic bone and/or into the sacrum. One skilled in the art will know various options for providing fixing devices for fixing a nail in a bone and may take one of these options at the implementation of the fixing device for fixing the nail at its second end in the first pelvic bone and/or in the sacrum. In particular, the fixing device can be constructed in such a way that it allows the nail to be fixed in a bone by means of the fixing device so that the nail is secured against displacement relative to the bone when a force is exerted on the nail in the direction of the axial extension of the nail. In particular, this force is one which is exerted on the pelvic ring in the longitudinal direction of the nail by the implant and which must be laterally applied on the anatomical parts of the pelvis, for instance the ilium and/or sacrum, for the arrangement of these parts in their required positions and for healing the fracture or for fixation of the pelvic ring anatomy. In particular, a second locking element may be provided as a fixing device, and a second transverse duct may provided at the nail so that the nail can be initially anchored at its second end to the locking element and thereafter fixed against twisting and displacement relative to a pelvic bone by an additional locking element. It goes without saying that several locking devices can be assigned to and several transverse ducts provided on one end of the bone, for fixation of the bone at that end.

An important advantage of the invention is that during implantation of the inventive implant, the nail can be initially fixed in a first pelvic bone and thereafter an external force can be exerted on the pelvic ring which causes the bones to be pressed against each other along the fracture site, so that the nail can then be securely fixed against twisting and displacement relative to the second pelvic bone by anchoring the locking element in the second pelvic bone.

Thus the pressure on the fracture site in the broken bone needs not be produced by the implant itself at the time of inserting the implant, but the pressure can be produced externally and the locking element is allowed to anchor the nail only in the position adjusted from the outside. This advantage is also obtained when the implant of the invention is inserted unilaterally, in which case the nail is initially fixed at its second end in a sacrum and is then anchored at its first end in a pelvic bone upon external compression of the pelvic ring in which the implant is positioned.

The implantation of the inventive implant can be carried out using for example a tunnel creation guide that can be coupled to the first end of the nail. The nail can be inserted into or passed through the tunnel with the aid of the tunnel creation guide if necessary, and the tunnel creation guide is adjusted to the nail of the implant so that the position and the drilling direction in which the at least one locking element is to be inserted into the human body so as to ensure anchorage of the nail in a pelvic bone, are set in advance for the surgeon. The tunnel creation guide may be connected to the nail especially during external compression of the pelvic ring.

A further important advantage of the invention is that the locking element can be inserted into the transverse duct in a way which enables angular stable locking of the locking element to the nail. Due to the anchorage of the locking element in the pelvic bone, the nail is arranged in an angular stable manner with respect to the pelvic bone. This effectively prevents bone fragments from being twisted against each other.

In particular, it is not necessary in the implant of the invention to pierce and/or penetrate the fracture site several times for its fixation. In fact, a single perforation of the sacrum is sufficient for producing the tunnel through which the nail is inserted or passed which can then be anchored at both ends thereof in one or several pelvic bones.

Therefore, the implant of the invention is particularly suited for fixation of a fracture in the iliosacral joint or in the sacrum. For fixation of such a fracture it is particularly advantageous that after fixation of the nail at the second nail end by means of a fixing device, anchorage of the locking element may be effected not in the sacrum or in the ilisacral joint, but instead in the pelvic bone, at least partially, so that there is no need to damage the fracture site. In fact, a simple and clean drill hole can be drilled through the fracture site, and the compression of the bone elements to be connected is not applied by the implant, but can be externally applied using for instance an external clamp that can be adapted to the implant, and/or a tunnel creation guide so that the thusly fixed position of the bone elements to each other can be fixed by anchorage of the locking element outside of the damaged bone. The implant of the invention is particularly constructed in such a way that the anchorage of the implant at its first nail end by means of the locking element does not cause any compression of the bone elements to be connected after fixation of the nail at its second nail end. The implant of the invention is particularly constructed in such a way that external compression, which is applied on the bones to be fixed after the nail has been fixed at its first end, is maintained with angular stability as a result of anchorage by means of the locking element.

The insertion or feeding of the nail through the tunnel and into or through the sacrum can be carried out using a cannulated nail, wherein said tunnel is drilled by way of a guidewire and the nail is then passed through the tunnel by way of said guidewire, which runs through the cannulation in the nail.

Preferably, the nail is constructed in such a way that is can be passed intra-ossarily through a pre-drilled tunnel through the S1 or S2 corridor of a sacrum, the nail particularly having a diameter of 7 mm to 10 mm and a length of 80 mm to 220 mm. In particular, the tunnel pre-drilled through the corresponding corridor may have a smaller diameter than the corresponding corridor to avoid damage to nerves outside of the corridor and/or to avoid the sacrum from being impaired. The S1 corridor is the corridor in the sacrum which is the largest and the highest and which offers the most bone substance so that it is particularly the S1 corridor where a penetration of the sacrum and a subsequent loading of the sacrum are possible without damaging the sacrum. Although the S2 corridor is smaller than the S1 corridor and provides less bone substance than the S1 corridor, it is larger than the S3 corridor, S4 corridor, and S5 corridor. All in all, the bone substance provided by the S2 corridor is still sufficient in most cases for allowing its penetration and thereafter implantation of a nail so that implantation of the nail without damage to the sacrum may be possible also in the S2 corridor. By providing a nail diameter of 7 mm to 10 mm and by keeping the diameter of the tunnel small, it is possible in particular to keep the balance between a preferably resistant construction of the nail and a preferably low load of the sacrum. In the majority of pelvic rings in adults, the provision of a nail length of 80 mm to 220 mm affords an arrangement of the nail through the sacrum in such a way that the nail ends are each positioned approximately in the center of the ilia surrounding the sacrum, wherein the "center" of the ilium means the center with reference to the lateral extension of the ilium if the pelvic ring is viewed from the front side. Where the implant of the invention is inserted bilaterally, nail lengths of 140 mm to 180 mm can be particularly expedient.

On the other hand, it also ensured that inventive implants with a shorter nail length can be inserted unilaterally by the nail not being passed through but instead only inserted into the sacrum and by the nail being fixed at its second end not in the ilium but instead in the sacrum. In this case, a nail length of 80 mm to 140 mm can be particularly expedient.

Advantageously, the transverse duct comprises an internal thread corresponding with a thread provided on a locking section of the locking element. The thread particularly enables the locking element being screwed together with the nail. It will be appreciated by the person skilled in the art that any type of thread allowing two elements to be screwed together may suit this purpose. In particular, the internal thread of the transverse duct can be constructed in the manner of a bone-screw thread corresponding with a bone-screw thread provided on a locking section of a locking element. Providing a metric thread as the internal thread in the transverse duct and as the external thread on the locking section can be particularly advantageous. By this metric thread, a fastening torque can be defined particularly well, and the lead of the thread can be determined in such a way that the locking between the nail and the locking element is as safe as possible.

In particular, a bone-screw thread can be provided at least on the anchoring section of the locking element. Said bone-screw thread facilitates anchorage of the locking element and thus also anchorage of the nail at the pelvic bone by simply screwing the locking element into a pelvic bone. The bone-screw thread can pass for instance from the anchoring section to the locking section without interruption. However, between the anchoring section and the locking section the thread may change, for example concerning the thread type or the lead of the bone-screw thread. It goes without saying that the anchoring section can comprise a bone-screw thread while the locking section is not a threaded construction but some other locking construction. The provision of threads on both the anchoring section and the locking section can however be advantageous in as much as the locking element during insertion into the transverse duct by turning and by applying a force in the direction of the passage can be locked to the nail and simultaneously anchored in a bone.

Advantageously, the diameter of the locking element in the locking section can be larger than in the anchoring section. This has the advantage that the anchoring section can be initially passed through the transverse duct without damaging the transverse duct because, corresponding to the larger diameter on the locking section, also the diameter of the transverse duct must be larger than that in the anchoring section.

Further, the locking mechanism between the locking section and the transverse duct can thus be formed completely independently from the anchoring mechanism between the bone and the anchoring section.

Further, the first anchoring section can be disposed on a first end of the locking element, the locking section being arranged behind the anchoring section if viewed from the first end of the locking element, and a section of the locking element which is pin-like and whose diameter is at least as large as the outer diameter of the locking element in the locking section, is arranged behind the locking section if viewed correspondingly.

Thus it is possible to feed the locking element with a first end through the transverse duct without damaging the interior of the transverse duct and thereafter lock the locking element with its locking section in said transverse duct. Because the diameter of the pin section is at least as large as the outer diameter of the locking section—the pin section being arranged behind the locking section if viewed from the first end—the pin section can be constructed in such a way that it precisely fits into the transverse duct. The precise fitting of the pin into the transverse duct and a certain longitudinal extension of the pin section provide for fixation between the locking element and the nail in which the angular stability is exceedingly good after the locking element has been locked to the nail via said locking section. For example, the locking section can comprise a thread and the pin can abut with its end facing the first end against the thread and/or a protrusion when the locking element is screwed into the transverse duct, so that the pin is urged against the corresponding element (thread/protrusion) of the nail when the locking element is tightly screwed to the nail. The provision of a corresponding thread having a corresponding lead as well as corresponding fastening torque provides particularly good connection between the locking element and the nail, for instance by a cold welding process carried out between the locking element and the nail.

Further, at least one of the locking elements can include a second anchoring section, wherein the locking section is arranged between said first and said second anchoring section and wherein said second anchoring section is constructed in the manner of a bone-screw thread. This construction enables the nail being locked to the locking element via the locking section, and the locking element being anchored in a bone both above and below the nail. The first and the second anchoring sections can be anchored for instance in an ilium. But it is also possible at the positioning of the implant to anchor at least one of these two anchoring sections in the sacrum or in a different bone of the pelvic ring, at least partially. The provision of the first and the second anchoring sections thus provides for good anchorage of the locking element above and below the nail, particularly in several different pelvic bones.

Advantageously, the diameter of the locking element in the second anchoring section is larger than the diameter of the locking element in the first anchoring section. Because the second anchoring section for anchoring the locking element to the nail needs not be fed through the transverse duct in the nail, the provision of a larger diameter in the second anchoring section does not cause any damage to the transverse duct in the nail. But this larger diameter can achieve particularly stable anchorage in the bone.

Advantageously, the nail can be designed anti-traumatizing on both ends thereof. This can be achieved for instance by caps being provided on each nail end. By correspondingly constructing the nail, the nail connections can remain functional and irritation of tissue surrounding the nail by said nail ends may be avoided.

Advantageously, the implant can comprise at least two locking elements, the nail including at least two transverse ducts for receiving a respective locking element. The fixing device for fixing the nail at its second nail end comprises one of said at least two locking elements, and between at least two of said transverse ducts a distance is provided such that after the nail has been passed through the sacrum, the locking elements can each be anchored in an ilium bone outside of the sacrum. Though the locking elements can be identical, this is not necessarily required. However, each of the locking elements is constructed so as to correspond to at least one of the transverse ducts in the nail. Because the fixing device comprises one of the locking elements, an angular stable anchorage of the nail in the pelvic bone is possible also at the second end of the nail. Moreover, the fixing device can comprise additional means such as a wedge-shaped construction of the nail at its second nail end or an additional locking element that corresponds for example with the first locking element comprised in the fixing device or with an additional transverse duct. In an advantageous embodiment, the implant comprises precisely two locking elements and precisely two transverse ducts in the nail, each of said transverse ducts being arranged close to the end of the nail. For example, at least 70% of the nail length can lie between these two transverse ducts of the nail. This construction of the locking element and the nail can provide for angular stable locking of the nail at both ends thereof in a pelvic bone in an easy manner if two locking elements and transverse ducts are correspondingly provided on each nail end. Thus the pelvic bones themselves may be fixed against each other in an angular stable manner. Angular stable fixation of the pelvic bones against each other may even ensure angular stable fixation of sacrum fractures along a fracture site in the sacrum by pressing the pelvic bones surrounding the sacrum against each other prior to anchorage of the locking element to the first nail end, whereby pressure is applied on the fracture site in the sacrum causing the sacrum fragments to engage each other along the fracture site so that angular stable fixation is achieved also of sacrum fragments when the nail is locked in the pelvic bone in an angular stable, pressure-loaded manner via said locking elements.

The advantages and embodiments described in the preceding paragraph are applicable in a corresponding manner also to an implant of the invention if at least two locking elements are provided, wherein the nail has at least two transverse ducts each for receiving one of the locking elements, wherein the fixing device for fixing the nail at its the second nail end comprises at least one of said two locking elements, wherein between at least two of said transverse ducts a distance is provided such that after the insertion of the nail into the sacrum, one of said locking elements can be anchored in the sacrum and one of said locking elements can be anchored outside of the sacrum in an ilium bone. The advantages will then be shown in context of the stabilization of bone fragments with unilateral insertion of the nail.

Generally, it should be noted that one or several transverse ducts can be arranged on both the first nail end and the second nail end and also at additional positions of the nail, and each transverse duct is assigned to a locking element in order to achieve good fixation of the implant and accordingly of the bone fragments to be stabilized.

Further, at least one or all of the transverse ducts may have an extension direction through the nail which forms an angle greater than 0°, preferably between 5° and 60°, to the vertical to the nail extension axis. By correspondingly tilting the extension direction of the transverse duct compared to the nail extension axis, particularly good anchorage of the locking element in the bone may be ensured and especially stable anchorage with regard to transverse and/or longitudinal loads of the nail.

Preferably, the nail may comprise at least two transverse ducts, the extension direction of the first transverse duct together with the extension direction of the second transverse duct in the direction of the nail extension axis and/or in the direction of the vertical to the nail extension axis forming an angle greater than 0°. Tilting the transverse ducts against each other may facilitate the implantation of the implant on the one hand. At least, this may facilitate anchorage of the locking element in at least one pelvic bone and/or in the sacrum. On the other hand, that tilting affords a preferably stable fixation of the nail in the at least one pelvic bone and/or in the sacrum and possibly also stable fixation of the pelvic bones against each other or stable fixation of a pelvic bone relative to the sacrum.

In a further embodiment, the extension direction of the first transverse duct together with the extension direction of the second transverse duct in the direction of the nail extension axis forms an angle between 5° and 175°, wherein the transverse ducts on the side of the nail from which the locking elements can be inserted into the transverse ducts are spaced from each other at a smaller distance than on the opposite side of the nail. After being locked to the nail, the locking elements in this embodiment form a V open towards the top and the bottom, the first ends of the locking elements with which the locking elements are fed through the transverse ducts being separated from each other a larger distance than the second ends of the locking elements. This embodiment affords good anchorage of the locking elements in at least one pelvic bone and/or in the sacrum. Moreover, with the use of a corresponding implant according to the invention, particularly good fixation of the pelvic bones to each other and/or of the sacrum to at least one pelvic bone may be implemented. In this context, it may be particularly advantageous for a good stabilization of bone fragments, especially of sacrum fragments, if the implant of the invention comprises two locking elements, each arranged on one end of the nail and respectively anchoring the nail in an ilium, said two locking elements mutually forming a V open towards the top and the bottom as explained above.

The invention further comprises a locking element for use in an inventive implant as described above, wherein the locking element includes an anchoring section and a locking section, the anchoring section is arranged on a first end of the locking element and the locking element is anchorable to a pelvic bone and/or sacrum by means of the anchoring section, and the locking section is disposed behind the anchoring section if viewed from the first end of the locking element.

Thus the locking element of the invention can be passed with its first end through a transverse duct of a nail and anchored in a pelvic bone and/or sacrum by means of the anchoring section passed through the nail while the locking section which is arranged behind the anchoring section can be locked to the nail. It should be taken into consideration that the anchoring sections needs not necessarily begin at the first end of the locking element. Instead, the first end of the locking element can be constructed in a different manner, for example in a functional manner, including for example a conical flattening that facilitates insertion into a transverse duct.

Advantageously, the diameter of the locking element in the locking section is larger than in the anchoring section. The anchoring section can thus be passed through a transverse duct without damaging the transverse duct, whereafter the anchoring section can be fixed with the nail in an angular stable manner via said transverse duct.

Advantageously, a section having a pin-like construction (pin section) and a diameter at least as large as the outer diameter of the locking element in the locking section is arranged behind the locking section if viewed from the first end. The outer diameter of the locking element in the locking section refers to the absolute outer diameter; therefore, when a thread is provided on the locking section, the outer diameter is not the shaft diameter but the outer diameter of the thread. The provision of a pin section may afford fixation with specifically good angular stability between a nail and an inventive locking element.

Further, the locking element may comprise a second anchoring section, the locking section being disposed between the first and second anchoring sections, and the second anchoring section being constructed in the manner of a bone-screw thread. The provision of said first and said second anchoring sections affords particularly good fixation of the locking element above and below the locking section thus providing particularly good anchorage of the nail in a pelvic bone and/or in the sacrum. Further, the diameter of the locking element in the second locking section can be larger than the diameter of the locking element in the first anchoring section and/or in the locking section. This larger diameter in the second anchoring section achieves particularly good fixation of the locking element in a bone, without causing damage to the transverse duct when the locking element is passed through a transverse duct in the nail.

Further, the locking element can comprise a connection element on the second end thereof, for coupling the locking element to a stabilization assembly of the lower lumbar vertebrae. By coupling said stabilization assembly to the locking element that is anchored in a pelvic bone and/or in the sacrum in an angular stable manner, the lumbar vertebrae can be particularly stably connected with the pelvic ring that is stabilized by the implant.

Advantageously, an axial bore is provided, through the locking element. The locking element can thus present a continuous through-bore, which axially extends throughout the locking element, namely from the first to the second end thereof. In particular, said through-bore may extend through the axial center of the locking element. Such a through-bore is frequently referred to as cannulation. In particular, a cannulation may serve the purpose of allowing the locking element for the implantation of the implant to be positioned via a guidewire. The guidewire can extend in said cannulation through the locking element so that for implantation said locking element can be sleeved on the guidewire and positioned in a targeted manner.

Advantageously, the locking element may comprise at least one cross bore. Said cross bores extend vertically to the axis of the locking element, at least with one directional component, and said axis connects the first end and the second end of the locking element. Said cross bores can for instance be transverse through-bores. However, said cross bores can also be bores which do not fully extend through the locking element. In particular, an inventive implant may comprise both an axial through-bore and cross bores, wherein said cross bores can be intersecting with said axial through-bore or lead into said axial through-bores. Said cross bores can for instance be beneficial for bone stabilization measures, particularly for anchoring the locking element in bones with poor bone quality. For example, bone cement can be filled into the cross bores which can escape from said cross bores after and/or during anchorage of the locking element and can stabilize the bone in which the locking element is anchored. In a locking element for example in which an axial through-bore is provided communicating with cross bores, the bone cement can be introduced into the cross bores via said axial through-bore. The bone cement can be supplied into the cross bores or in the axial through-bore for instance by injection.

The invention also relates to a nail for use in an inventive implant as described above.

In one embodiment, the nail of the invention comprises a transverse duct on one nail end, while the nail can be inserted with its second nail end through a tunnel into a sacrum and fixed in the sacrum or passed through the sacrum and fixed in a first pelvic bone in such a manner that said transverse duct is situated in an ilium region after the nail has been inserted or passed-through and fixed.

In a further embodiment, the nail comprises at least two transverse ducts, a distance being provided between said transverse ducts such that the nail can be passed through a tunnel in the sacrum in such a way that the transverse ducts are each situated in an ilium region after the nail has been passed through said tunnel. Thus the nail of the invention can be positioned in a sacrum in such a way that it may be fixed to an ilium on each side of the sacrum by means of a locking element. This provides for particularly good fixation with good angular stability of the nail on both sides thereof in an ilium and accordingly of the ilium bones against each other. This can be beneficial especially for the stabilization of sacrum fractures because in this way the sacrum itself, which is arranged between the left and right human ilium, can be fixed in a stable, particularly in an angular stable manner.

In a further embodiment, the nail of the invention comprises at least two transverse ducts, a distance being provided between said transverse ducts such that the nail can be inserted through a tunnel into a sacrum in such a way that at least one of the transverse ducts is situated in an ilium region after the nail has been inserted through the tunnel. Thus the nail can provide for angular stable fixation of the sacrum relative to an ilium bone which is particularly good, whereby the bone fragments to be stabilized can be fixed against each other particularly well and in angular stable manner.

Advantageously, the nail comprises at least on one end thereof a coupling device for coupling a compression clamp and/or a tunnel creation guide. Thus the nail can be inserted by surgery into the tunnel with the aid of the tunnel creation guide, which thus affords a simple and precise operation technique with the aid of the nail of the invention.

Advantageously, a hole can be drilled axially through the nail. Accordingly, the nail may comprise a continuous through-bore which fully extends axially through the nail, namely from its first nail end to its second nail end. In particular, said bore can extend through the axial center of the nail. Such a bore is frequently referred to as cannulation. A cannulation may particularly serve the purpose of allowing the nail for implantation of an implant of the invention to be positioned via a guidewire. The guidewire can run in said cannulation through the nail so that for implantation, the nail can be sleeved on the guidewire and positioned in a targeted manner.

The invention further relates to a method for implantation of an implant according to the invention for stabilization of pelvic ring fractures, wherein the sacrum is pre-drilled with a tunnel, wherein a nail which is encompassed by the implant is passed through the tunnel through the sacrum or is inserted through the tunnel into the sacrum, wherein the nail after being passed-through or inserted, is fixed at its second end in a first pelvic bone and/or in the sacrum, wherein after fixation of the nail at its second end a compression pressure is externally applied on the pelvic ring, whereby the pelvic ring is compressed in the region of the longitudinal extension of the nail, wherein the nail is anchored at its first end in a second pelvic bone in such a way that the nail is secured against twisting and displacement relative to the second pelvic bone. Advantageously, anchorage of the nail is effected in the second pelvic bone after the compression pressure has been applied. Advantageously, the compression pressure is maintained unchanged during anchorage of the nail in the second pelvic bone. Advantageously, the compression pressure is applied in one direction of the axial extension of the nail, at least in one component. Concerning the construction of the abovementioned components, reference is made to the entire contents of the remaining statements in the context of the invention.

In one embodiment, the implantation is carried out unilaterally, wherein the nail is introduced into the tunnel pre-drilled in the sacrum and is fixed at its second nail end in the sacrum against displacement in the direction of its axial extension, whereupon the compression pressure is applied and the nail is secured at its first nail end against twisting and displacement relative to the second pelvic bone by means of the locking element.

In one embodiment, the implantation is carried out bilaterally, wherein the nail is passed through the tunnel pre-drilled in the sacrum and is fixed at its second nail end in the first pelvic bone at least partly outside of the sacrum, against displacement in the direction of its axial extension, whereupon the compression pressure is applied and the nail is secured at its first nail end against twisting and displacement relative to the second pelvic bone by means of the locking element.

Figure 2:
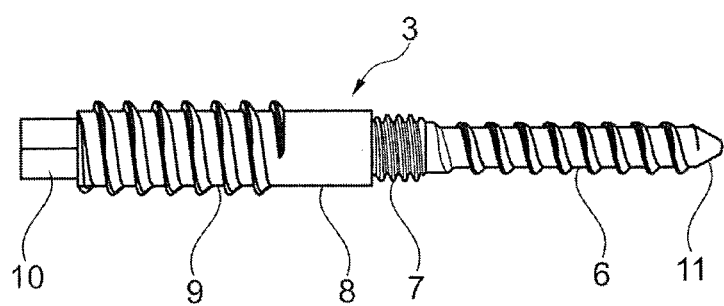
Figure 3:
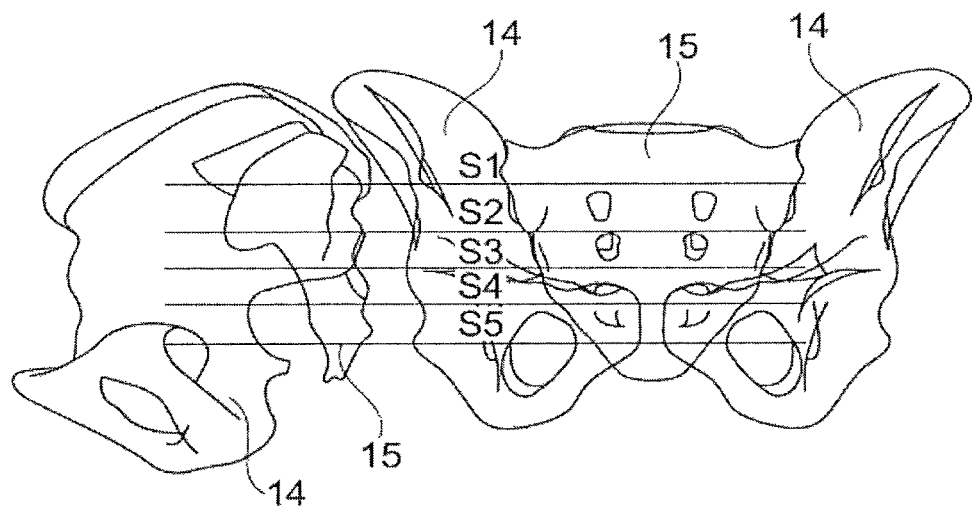
Figure 4:
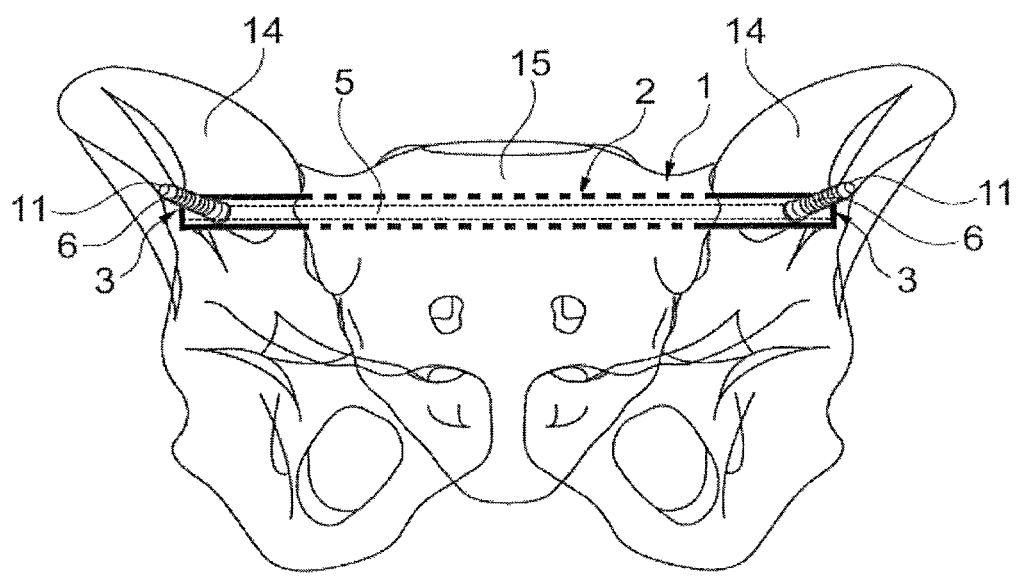
Figure 5:
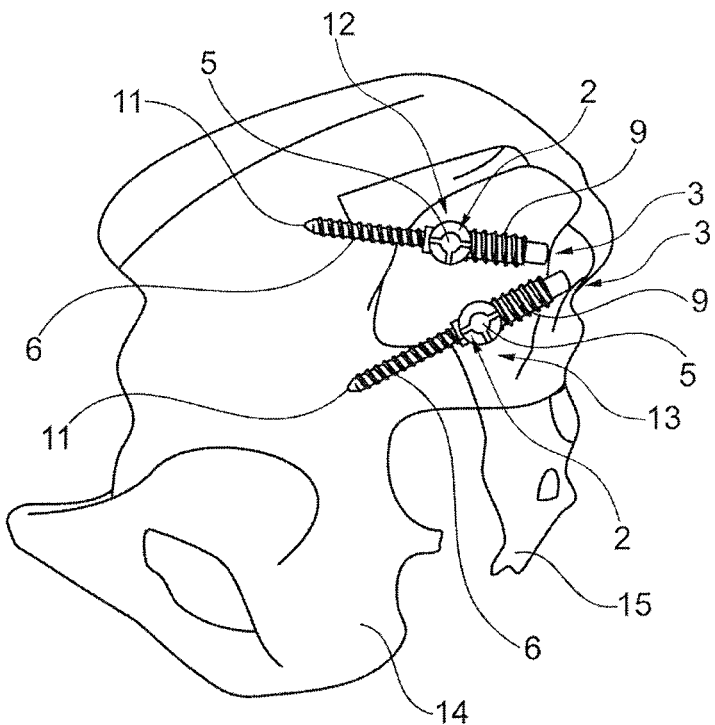
Figure 6:
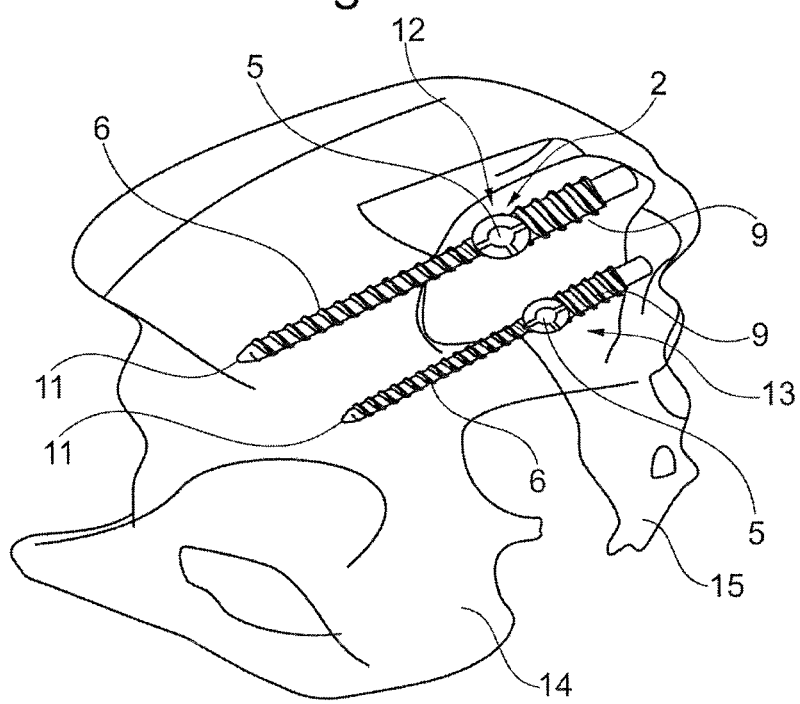
Figure 7:
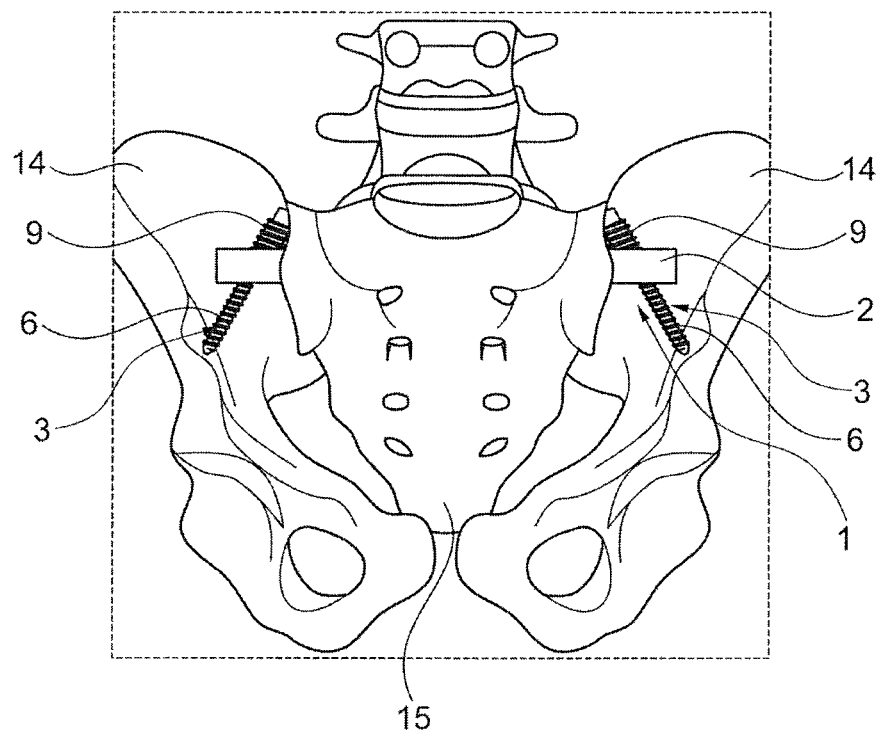
Figure 8:
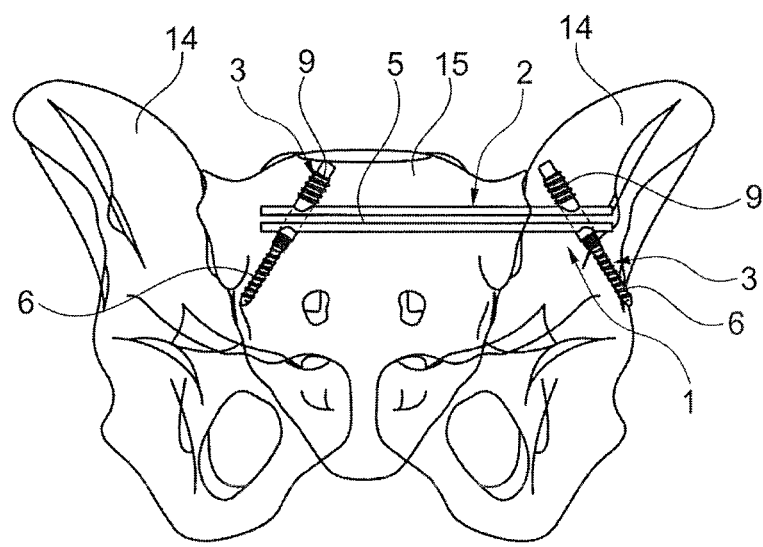
Figure 9:
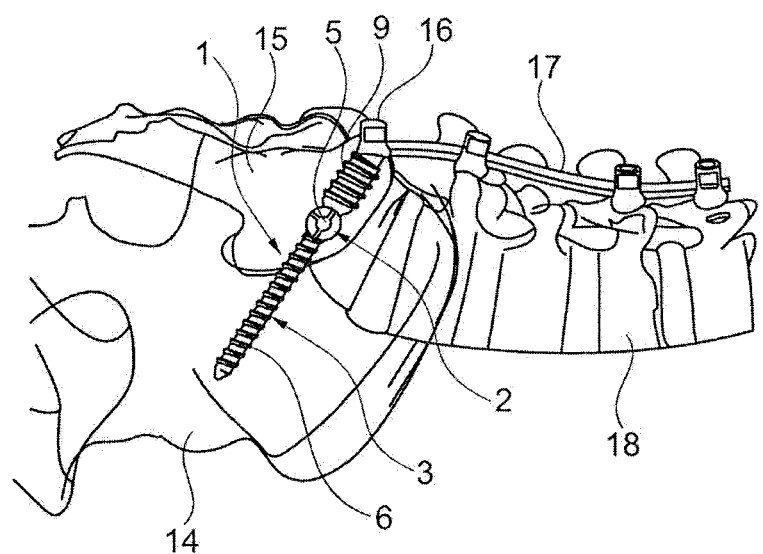
Figure 10:
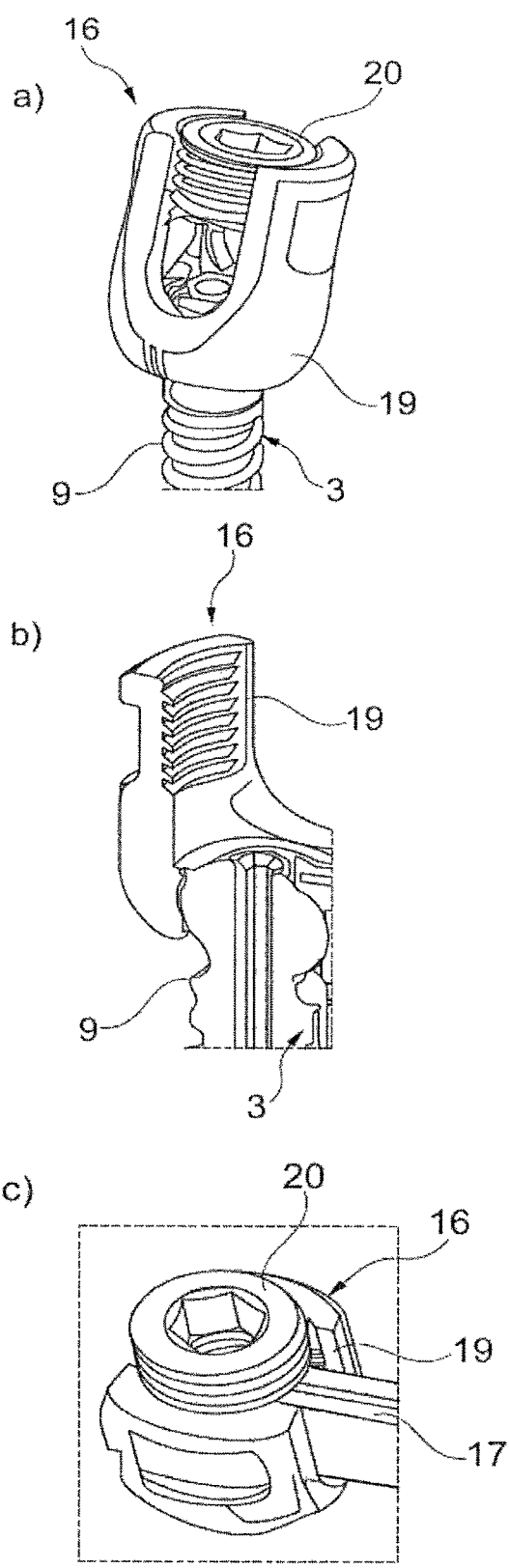

In the following, embodiments of the invention will be described in more detail with reference to the attached drawing figures, wherein it is shown by:

FIG. 1 a schematic diagram of an implant according to the invention;

FIG. 2 a schematic diagram of a locking element according to the invention;

FIG. 3 a schematic diagram of a front and lateral view of a human pelvic ring;

FIG. 4 a schematic diagram of the front view of a human pelvic ring positioned with an implant according to the invention;

FIG. 5 a schematic diagram of a lateral view of a human pelvic ring positioned with two implants according to the invention;

FIG. 6 a schematic diagram of a lateral view of a human pelvic ring positioned with two implants according to the invention;

FIG. 7 a schematic diagram of a lateral view to a human pelvis positioned with an implant according to the invention, corresponding to the front view of FIG. 6;

FIG. 8 a schematic diagram of the front view of a human pelvis carrying the implant according to the invention;

FIG. 9 a schematic diagram of a lateral view of the human pelvis with the lower end of the lumbar vertebral column carrying an implant according to the invention to which a stabilization assembly of the lumbar vertebral column is coupled;

FIG. 10 a schematic diagram of the coupling device between the implant and the stabilization assembly in accordance with FIG. 9.

FIG. 1 shows an implant according to the invention which comprises a nail 2 as well as two locking elements 3. In the nail 2, two cannulations 5 and two transverse ducts 4 are arranged. The cannulation 5 in the nail 2 is illustrated in FIG. 1 in a sectional view. In fact, the nail 2 of the implant of the invention shown in FIG. 1 is constructed in the manner of an elongate cylinder, said cylinder comprising as cannulation 5 a bore that is bored through the longitudinally extending axis of the cylinder. This bore and thus the diameter of the cannulation 5 amount to 3.5 mm in the illustrated embodiment. In other embodiments, corresponding cannulations 5 with a different diameter, e.g. a diameter between 1 mm and 5 mm, could be provided. When choosing the diameter of the cannulation 5, the same may be specifically adapted to the diameter of the nail 2 and/or the diameter of a guidewire required for the implantation of the implant according to the invention.

The transverse ducts 4 in the nail 2 are shown by the dotted lines in FIG. 1. Said transverse ducts 4 accordingly traverse the nail 2 over its entire diameter and are designed as a straight tunnel. In other embodiments of the implant of the invention, said transverse ducts 4 may also be curved along their extension direction, this curved configuration benefiting for instance the clamping and thus angular stable fixation between a locking element 3 and the nail 2. The extension direction of each of the two transverse ducts 4 of the nail 2 forms an angle to the vertical of the nail extension direction. This angle is identical for both transverse ducts 4 and amounts to about 20°. The extension directions of both transverse ducts 4 span a plane such that the two extension directions form an angle greater than 0° in the direction of the extension axis of the nail 2, but not in the direction of the vertical to the extension axis of the nail 2. In other embodiments which are not illustrated in FIG. 1, it is of course also possible for the extension directions of the transverse ducts 4 which are provided in the nail 2, forming an angle greater than 0° both in the direction of the extension axis of the nail 2 and in the direction of the vertical to the extension axis of the nail 2 or also only in the direction of the vertical to the extension axis of the nail 2. Thus it is possible for the extension directions of the transverse ducts 4 not being arranged in one plane.

The locking elements 3 which are comprised in the inventive implant according to FIG. 1 are shown in detail in FIG. 2. Said two locking elements 3 in the implant 1 according to FIG. 1 are identically constructed. In other embodiments which are not illustrated, the locking elements 3 provided in an inventive implant 1 can also be differently constructed, at least partially. It is merely required that one locking element 3 respectively corresponds with one of the transverse ducts 4.

The locking element 3 according to the invention which is used along with the inventive implant 1 according to FIG. 1 has a first anchoring section 6, a locking section 7, a pin section 8, and a second anchoring section 9. On its first end, the locking element 3 is conically flattened so that the insertion of the locking element 3 into a transverse duct 4 of the nail 2 can be carried out more easily. On its second end, the locking element 3 has a tool connector 10. The tool connector 10 is constructed in the manner of a hexagon so that the locking element 3 can be implanted using a hexagon screw tool.

The locking element 3 is constructed in the manner of a screw comprising different thread sections. The first anchoring section 6 comprises a bone-screw thread with which the locking element 3 can be screwed into a bone after the locking element has been passed through the associated transverse duct 4. The first anchoring section 6 is followed by the locking section 7, which in the illustrated embodiment is offset from the first anchoring section 6 and comprises a metric thread. The diameter of the locking element 3 in the locking section 7 is larger than the diameter in the first anchoring section 6, and the diameter of the locking section 7 is adapted to the inner diameter of the transverse duct 4 of a nail 2 assigned to the locking element 3. This assigned transverse duct 4 has a metric thread that corresponds with the metric thread provided on the locking section 7. Accordingly, locking between the nail 2 and the locking element 3 is effected by a screw connection of the locking element 3 with the metric thread in the transverse duct 4 of the nail 2 via the metric thread in the locking section 7.

Because the diameter of the locking element 3 in the first anchoring section 4 is smaller than in the locking section 7, the locking element 3 can be initially passed with its first end 11 through the transverse duct 4, without the bone-screw thread in the first anchoring section 6 and the metric thread in the transverse duct 4 causing damage to one another. Thereafter, fixation between the nail 2 and the locking element 3 is effected by screwing the locking section 7 to the transverse duct 4. Advantageously, during the entire process of feeding the locking element 3 through the transverse duct 4, said locking element is continuously turned in order that the bone-screw thread can screw into a bone at the first anchoring section 6 as soon as the first end 11 of the locking element 3 meets a bone. Anchorage of the locking element 3 can be effected simultaneously with locking in the course of this turning action.

Angular stable locking between the first locking element 3 and the nail 2 in the embodiment illustrated in FIG. 1 is particularly promoted by a pin section 8 provided behind the locking section 7 if viewed from the first end of the locking element 3, the diameter of pin section 8 being larger than the diameter of the locking section 7. In the locking process between the locking element 3 and the nail 2, the pin section is pressed against the metric thread, which is arranged in the transverse duct 4. Because the diameter of the pin section 8 is larger than the inner diameter of the thread in the transverse duct 4, the pin section 8 cannot slide through the transverse duct 4. Instead there is established a rigid, angular stable connection between the nail and the locking element 3. In the described preferred embodiment, the transverse duct 4 is constructed in such a way that it comprises a non-threaded section on the end thereof which is associated with the pin section 8, and the non-threaded section can receive the pin section 8 circumferentially in a form-locking manner thus providing particularly stable fixation between the nail 2 and the locking element 3.

A second anchoring section 9 is arranged behind the pin section 8 if viewed from the first end 11 of the locking element 3. The second anchoring section 9 comprises a bone-screw thread. For anchoring the locking element 3 by means of the first anchoring section 6 and for locking by means of the locking section 7, the locking element is turned. Thus also the second anchoring section 9 is anchored in a bone as a result of the bone-screw thread on the second anchoring section 9 cutting into a bone. Thus the locking element 3 is respectively anchored with its first anchoring section 6 and second anchoring section 9 in a bone, after the process of feeding the locking element 3 through the transverse duct 4 of the nail 2 is completed. Additionally, the locking element 3 is locked to the nail 2. As can be seen in FIG. 1, the anchorages are respectively arranged above and below the locking between the locking element 3 and the nail 2. This ensures particularly good fixation of the nail 2, which is fixed in angular stable manner by the locking element 3, in a pelvic bone.

FIG. 3 shows the human pelvis comprising the sacrum 15 and an ilium 14 on each side of the sacrum 15. The sacrum 15 comprises five vertebrae that are fused together. Correspondingly, the sacrum 15 has five regions in which the sacrum 15 is formed as a continuous bone throughout its width. The regions are referred to as S1, S2, S3, S4, and S5 corridor and are illustrated in FIG. 3. An implant according to the invention is preferably positioned in one of these five regions or corridors. In the case of a sacrum fracture or a fracture of the iliosacral joint, an implant according to the invention can be positioned in the pelvic ring in such a way that the nail is intra-ossarily positioned through the sacrum in one of the stated corridors, wherein the nail 2 extends beyond the sacrum on both sides so that both ends of the nail 2 can be anchored in a respective ilium.

FIG. 4 shows a human pelvic ring according to FIG. 3 carrying an inventive implant 1 according to FIG. 1. The inventive implant 1 has been positioned in the S1 corridor with sections inside the sacrum 15. The nail 2 of the implant 1 extends beyond the sacrum 15 on both sides of the sacrum so that the nail 2 can be anchored at both ends thereof in an ilium 14 via the combination between a transverse duct 4 and a locking element 3. In the example illustrated in FIG. 4, the locking elements 3 are each screwed through the ilium from the rear to the front. It is apparent from FIG. 4, that the locking elements 3 exert no or only very low pressure on bones in the pelvic ring in a direction along the extension axis of the nail 2, even during implantation. In fact, the locking elements 3 exclusively serve the anchorage of the nail 2 in an ilium for angular stable fixation between the nail 2 and the ilium. For carrying out an implantation as shown in FIG. 4, first of all a tunnel is drilled through the S1 corridor of the sacrum 15. Then the nail 2 is passed through this tunnel and fixed at its second end to a first ilium 14 by means of a locking element 3 in combination with said transverse duct 4. Thereafter, an external force is applied on the pelvis in order to press the bone fragments together and to correctly position the bone fragments. The nail 2 is anchored at its first end in the second ilium 14 using an additional locking element 3 in combination with an additional tunnel 4. It will be apparent to a person skilled in the art that the implant according to the invention is particularly beneficial in the case of fractures of the sacrum 15 and of the iliosacral joint because the fragments of the sacrum 15 or of the iliosacral joint can be stabilized against each other very well by the rigid, angular stable fixation of the two ilia 14, which achieves very good healing of such fractures.

FIG. 5 is a lateral view of a human pelvis with two implants 12, 13 according to the invention. The upper implant 12 in FIG. 5 is positioned through the S1 corridor of the sacrum, the lower implant 13 in FIG. 5 is positioned through the S2 corridor of the sacrum 15. The extension direction of the locking elements of the upper implant 12 is tilted with respect to the extension direction of the locking elements 3 of the lower implant 13. It should be considered that the extension direction of the locking elements 3 or the screwing-in direction of the locking elements 3 can be freely chosen during the implantation, depending on medical aspects. A medical indication for the screwing-in direction of the locking element 3 may be for example that the locking elements 3 with their anchoring sections 6, 9 have to be screwed into a bone substance which is a stable as possible. But also the progression of nerves and other medical indications may play a part in the orientation of the locking elements 3. In FIG. 5, the cross-section of the nail can be seen. The nail has a cannulation 5 and is formed as a hollow cylinder around said cannulation 5. FIG. 5 also shows the coupling device of the nail which serves for coupling a tunnel creation guide.

FIG. 6 shows a further example of inventive implants 12, 13 positioned in a pelvic ring.

In the implantation situation illustrated in FIG. 6, the implant 12 is positioned in such a way that the nail 2 of the implant 12 extends through the S1 corridor of the sacrum 15. Compared to the implantation situation of an implant 1, 12 in the S1 corridor of the sacrum 15 as shown in the FIGS. 4 and 5, the locking elements 3 are oriented in a different extension direction. Compared to the implantation situation illustrated in FIG. 5, the implant 13 is positioned only slightly tilted. Compared to the implants 12, 13 shown in FIG. 5, the locking elements 3 of the implants 12, 13 shown in FIG. 6 have different lengths. It is apparent that the specialist may adapt the respective geometrical features of locking elements 3 and implants 1, 12, 13 with regard to the respective implantation situation that is provided for the inventive implant 1, 12, 13.

In FIG. 6, the locking elements 3 of the two implants 12, 13 are screwed together from the upper rear side towards the lower front side. In this case, the second anchoring section of the locking elements 3 can be anchored not only in the ilium 14 but also in the sacrum 15. Altogether, this affords exceptionally good stabilization of the sacrum 15 with respect to the ilium 14 and exceptionally good anchorage of the nail 2 in the overall pelvic ring. A corresponding anchorage of the locking elements 3 in the sacrum 15 and in the ilium 14 can be seen in FIG. 7. FIG. 7 is a front view of a human pelvis in which an inventive implant 1 is positioned in sections in the S1 corridor of the sacrum. The implantation situation of the implant 1 illustrated in FIG. 7 corresponds to the implantation situation of the implant 12 illustrated in FIG. 6.

FIG. 8 is a front view of a human pelvis carrying the inventive implant 1 in one embodiment. Compared to the embodiments shown in the FIGS. 4 to 7, a shorter nail 2 is provided in the inventive implant 1 according to FIG. 8. The inventive implant comprises two locking elements 3, and the nail 2 of the implant 1 includes two transverse ducts 4. The fixing device of the inventive implant 1 is implemented by the co-action of one of the said two locking elements 3 with one of the said two transverse ducts 4. In FIG. 8, the inventive implant 1 is inserted unilaterally. The nail 2 is introduced intra-ossarily into the sacrum 15 through a tunnel pre-drilled in the sacrum 15. The nail 2 is fixed in the sacrum 15 by means of one of the two locking elements 3. Further, the nail 2 is anchored in an ilium 14 by means of the other one of the two locking elements 3. At the implantation of the implant 1 according to FIG. 8, the nail 2 is first inserted into the tunnel in the sacrum 15 and is then fixed at its second end in the sacrum 15 by means of a locking element 3. Thereafter, the pelvic ring is compressed from the outside, for instance by means of a compression clamp or a tunnel creation guide. The compression clamp or the tunnel creation guide can be coupled to the first nail end, which is situated in an ilium region after the nail 2 has been inserted through the tunnel into the sacrum 15 and fixed in the sacrum 15. Thus it can be ensured that the second one of the two locking elements 3 can be unerringly passed through the second one of the two ducts 4 and anchored in the ilium 14 upon application of the compression pressure on the pelvic ring from the outside. The implant 1 shown in FIG. 8 provides angular stable fixation of the sacrum 15 with respect to the ilium bone 14. In FIG. 8, the nail 2 is inserted through a tunnel in the S1 corridor of the sacrum 15 into the sacrum 15. Depending on the specific circumstances in this individual case, especially with regard to the nature and site of the fracture as well as the geometry of the human pelvic ring in which the inventive implant 1 according to FIG. 8 is to be positioned, the implant 1 may be implanted in various positions in the pelvic ring, and the extension directions of the transverse duct 4 in the nail 2 can be determined as required. Possible embodiments and options for implantation as described in connection with the FIGS. 1 to 7 can be correspondingly applied for the implant 1 according to FIG. 8, which is suitable for unilateral insertion.

FIG. 9 is a lateral view of the human pelvis with the lower end of the lumbar vertebral column, wherein an inventive implant 1 is positioned in the pelvis and a stabilization assembly is coupled to the lower lumbar vertebral column 18. The implant 1 shown in FIG. 9 substantially comprises the same features as the implant 12 in S2 corridor shown in FIG. 6. The implant 1 according to FIG. 9 additionally comprises a connection element 16 by which a stabilization element 17 of a stabilization assembly of the lower lumbar vertebral column 18 may be coupled to the implant 1. The connection element 16 is arranged on the second end of the locking element 3 and thus on that end of the locking element 3 where the second anchoring section 9 is situated. By providing the stabilization assembly for the lower lumbar vertebral bodies and by coupling that stabilization assembly to the inventive implant 1, a stable arrangement of the pelvic ring with respect to the lower lumbar vertebral column 18 is afforded. This ensures perfect immobilization of affected sites in the pelvic ring and/or in the lower lumbar vertebral column 18.

The connection element 16, which is comprised in the implant 1 illustrated in FIG. 9, is shown in detail in the FIGS. 10a), 10b), and 10c). The connection element 16 comprises a retaining body 19 and a screw 20, which can be screwed into the retaining body 19. Correspondingly, the retaining body 19 has an internal thread on the end thereof turned away from the locking element 3. The connection element 16 includes a seat that corresponds with the second end of the locking element 3. The locking element 3 can thus be accurately fitted into the seat of the connection element 16. In the illustrated embodiment, the seat of the retaining body 19 and the second end of the locking element 3 are each rounded in some areas so that the extension direction of the connection element 16 is not required to run parallel to the extension direction of the locking element 3, but the connection element 16 can be arranged tilted with respect to the locking element 3 (see FIG. 10a)). This ensures certain flexibility between the stabilization assembly of the lower lumbar vertebral column and the implant 1 according to the invention. In the illustrated embodiment, tilting between the connection element 16 and the locking element 3 is ensured by the locking element 3, which includes a circumferential notch close to its second end into which the retaining body 19 may extend in a condition tilted with respect to the locking element 3. Other embodiments, which are not illustrated, can differ from the embodiment shown in FIG. 10 for instance by the fact that no rounding is provided on the locking element 3 and/or on the seat of the retaining body 19 so that a corresponding flexibility is not guaranteed.

The retaining body 19 includes a recess through which a stabilization element 17 of a stabilization assembly can be passed. FIG. 10c) shows a connection element 16 with a stabilization element 17 passed through the recess thereof. Fixation of the stabilization element 17 with respect to the connection element 16 is effected by the screw 20 being screwed into the retaining body 19 via the internal thread on the retaining body 19 while producing a contact pressure on the stabilization element 17. On the outer side of the retaining body 19 a tool connector is provided to which a tool can be attached so that the retaining element 19 can be prevented from twisting during screwing the screw 20 into the retaining body 19 and a sufficient fastening torque may be applied on the screw without causing twisting of the retaining body 19. Other embodiments can differ from the embodiment illustrated in FIG. 10 for instance by the tool connector and/or the recess being differently constructed.

The above-described embodiments show that the implant 1 according to the invention can be used in a very simple and versatile manner in an implantation for stabilization of pelvic ring fractures. The embodiments illustrate various examples of approaches for implanting an inventive implant 1, 12, 13 in a human pelvic ring. It will be understood that several implants 1, 12, 13 according to the invention may be used for stabilization of pelvic ring fractures. In addition, where only one implant is used, each of the implantation situations that have been described can be realized in relation to that implant, particularly regarding the position of the implant 1, 12, 13. Further, an implant according to the invention can be used not only in a human pelvic ring but also in a pelvic ring of mammals.

In particular, with the implant 1 according to the invention, implantations can be carried out in due consideration of the specific individual medical case while avoiding overstraining of the contacts of bone fragments along the fracture site. In addition, as a result of angular stable locking between the locking element 3 and the nail 2, the overall implant 1 is angular stable and stable against twisting so that the implant 1 particularly provides angular stable fixation of pelvic ring fractures. In the same manner, the invention may be used for carrying out an arthrodesis at degenerative instabilities and/or arthroses of the sacroiliac joint.

LIST OF REFERENCE NUMBERS 1 implant
2 nail
3 locking element
4 transverse duct
5 cannulation
6 first anchoring section
7 locking section
8 pin section 9 second anchoring section
10 tool connector
11 first end of locking element
12 implant in S1 corridor
13 implant in S2 corridor
14 ilium
15 sacrum
16 connection element
17 stabilizing element
18 lower lumbar vertebral column
19 retaining body
20 screw

What is claimed is:

1. An implant system, the implant system comprising:
a pelvic implant configured to stabilize at least one pelvic ring fracture in a pelvic ring, the pelvic implant including
   a nail for intra-ossary implantation, the nail having a form of an elongated cylinder, and having a first end, a second end and a nail length,
   a fixing device,
   a first locking element for relative fixation of pelvic bones with respect to the nail,
wherein the fixing device comprises a second locking element,
wherein the nail is configured to be passed intra-ossarily through a tunnel pre-drilled through a sacrum or intra-ossarily inserted into a tunnel pre-drilled in the sacrum without providing a fixation of the pelvic ring fracture in a direction of an axial extension of the nail,
wherein the nail has a first transverse duct for receiving the first locking element on its first end and a second transverse duct for receiving the second locking element on its second end, wherein the two transverse ducts are spaced apart by at least 70% of the nail length,
wherein each of the locking elements comprises an anchoring section configured to provide anchoring of the locking element in pelvic bone, and a locking section that corresponds with one of the transverse ducts of the nail in such a manner that the locking element is lockable to the nail in an angular stable manner,
wherein the nail is configured to be fixed at its second end in a first pelvic bone and/or in the sacrum by the fixing device after having being passed through or into the sacrum,
wherein the nail is configured to be fixed against twisting and displacement at its first end relative to a second pelvic bone by the first locking element to provide for angular stable locking of the nail at both ends thereof in a pelvic bone and to maintain in an angular stable manner an external force exerted after fixation of the nail at its second end on the pelvic ring in the direction of the axial extension of the nail,
wherein at least one of the transverse ducts comprises an internal thread that engages directly with a thread provided on the locking section of at least one of the locking elements,
wherein the internal thread of the at least one transverse duct which engage directly with the thread provided on the locking section of at least one of the locking elements is formed by the elongated cylinder of the nail,
wherein the first transverse duct has a first transverse duct extension direction through the nail, wherein the first transverse duct extension direction is fixed by the nail, and wherein the second transverse duct has a second transverse duct extension direction through the nail, wherein the second transverse duct extension direction is fixed by the nail, and
wherein the first transverse duct extension direction and the second transverse duct extension direction are arranged such that, when the first locking element is received by the first transverse duct and the second locking element is received by the second transverse duct, the first locking element and second locking element converge towards each other outside the nail on a first side of the nail and diverge away from each other outside the nail on a second side of the nail opposite the first side of the nail.

2. The implant system according to claim 1, wherein the nail is configured to be passed intra-ossarily through a tunnel pre-drilled through a S1 or S2 corridor of the sacrum, the nail having a diameter of 7 mm to 10 mm and the nail length being 80 mm to 220 mm.

3. The implant system according to claim 1, wherein the nail is configured to be inserted intra-ossarily into a tunnel pre-drilled in a S1 or S2 corridor of the sacrum, the nail having a diameter of 7 mm to 10 mm and the nail length being 80 mm to 220 mm.

4. The implant system according to claim 1, wherein a bone-screw thread is provided at least on the anchoring section of at least one of the locking elements.

5. The implant system according to claim 1, wherein a diameter of at least one of the locking elements in the locking section is larger than a diameter in the anchoring section of the at least one of the locking elements.

6. The implant system according to claim 1, wherein, for at least one of the locking elements,
the anchoring section is arranged on a first end of the at least one of the locking elements, wherein the locking section is arranged behind the anchoring section if viewed from the first end of the at least one of the locking elements, wherein a section of the at least one of the locking elements, which is constructed as an non-threaded pin section having a diameter that is at least as large as an outer diameter of the at least one of the locking elements in the locking section, is arranged behind and adjacent the locking section if viewed from the first end of the at least one of the locking elements.

7. The implant system according to claim 1, wherein the anchoring section of at least one of the locking elements provides a first anchoring section, and wherein the at least one of the locking elements further comprises a second anchoring section, wherein the locking section is arranged between the first and the second anchoring sections and wherein the second anchoring section is constructed in the manner of a bone-screw thread.

8. The implant system according to claim 7, wherein a diameter of the at least one of the locking elements in the second anchoring section is larger than a diameter of an anchoring element in the first anchoring section and/or in the locking section.

9. The implant system according to claim 1, wherein the nail is configured on both ends in an anti-traumatizing manner.

10. The implant system according to claim 1, wherein at least one or both of said transverse ducts have an extension direction through the nail which forms an angle greater than 0° to a vertical to a nail extension axis.

11. The implant system according to claim 1, wherein an extension direction of the first transverse duct together with an extension direction of the second transverse duct in a direction of a nail extension axis and/or in a direction of a vertical to a nail extension axis form an angle greater than 0°.

12. The implant system according to claim 11, wherein the extension direction of the first transverse duct together with the extension direction of the second transverse duct in the direction of the nail extension axis form an angle of between 5° and 175°, wherein the ducts on a side of the nail from which the locking elements are insertable into the ducts are spaced from each other at a smaller distance than on an opposite side of the nail.

13. The implant system according to claim 1, wherein, for at least one of the locking elements,
the anchoring section is arranged on a first end of the at least one of the locking elements and the at least one of the locking elements is configured to be anchored to a pelvic bone and/or sacrum by the anchoring section, wherein the locking section is arranged behind the anchoring section if viewed from the first end of the at least one of the locking elements.

14. The implant system according to claim 13, wherein the at least one of the locking elements has a diameter larger in the locking section than in the anchoring section.

15. The implant system according to claim 14, wherein the at least one of the locking elements, viewed from the first end, has a section arranged behind and adjacent the locking section being constructed as an non-threaded pin section having a diameter which is at least as large as an outer diameter of the at least one of locking elements in the locking section.

16. The implant system according to claim 13, wherein the anchoring section of the at least one of the locking elements provides a first anchoring section, and wherein the at least one of the locking elements further comprises a second anchoring section, wherein the locking section is arranged between the first and the second anchoring sections and wherein the second anchoring section is constructed in the manner of a bone-screw thread.

17. The implant system according to claim 16, wherein a diameter of the at least one of the locking elements in the second anchoring section is larger than a diameter of the at least one of the locking elements in the first anchoring section and/or in the locking section.

18. The implant system according to claim 13, wherein the at least one of the locking elements further comprises a connection element on a second end of the at least one of the locking elements, for coupling the locking element to a stabilization assembly for lower lumbar vertebral bodies.

19. The implant system according to claim 13, wherein the at least one of the locking elements comprises an axial bore provided through the at least one of the locking elements.

20. The implant system according to claim 13, wherein the at least one of the locking elements comprises at least one cross bore.

21. The implant system according to claim 1, wherein the nail is configured to be inserted, without providing a fixation of the pelvic ring fracture in the direction of the axial extension of the nail, with its second nail end through a tunnel into a sacrum and fixed in the sacrum or passed through the sacrum and fixed in a first pelvic bone in such a manner that the first transverse duct is situated in the ilium region after the nail has been inserted or passed-through and fixed at its second nail end.

22. The implant system according to claim 21, wherein the nail comprises a coupling device at least on one of its ends, for coupling a compression clamp and/or a tunnel creation guide.

23. The implant system according to claim 21, wherein an axial bore is provided through the nail.

24. The implant system according to claim 1, wherein:
the first locking element has a first locking element longitudinal axis;
the second locking element has a second locking element longitudinal axis; and
the first locking element longitudinal axis and the second locking element longitudinal axis extend in a common plane.

25. An implant system, the implant system comprising:
a pelvic implant configured to stabilize at least one pelvic ring fracture in a pelvic ring, the pelvic implant including
a nail for intra-ossary implantation, the nail having a first end, a second end and a nail length,
a fixing device,
a first locking element for relative fixation of pelvic bones with respect to the nail,
wherein the fixing device comprises a second locking element,
wherein the nail is configured to be passed intra-ossarily through a tunnel pre-drilled through a sacrum or intra-ossarily inserted into a tunnel pre-drilled in the sacrum without providing a fixation of the pelvic ring fracture in a direction of an axial extension of the nail,
wherein the nail has a first transverse duct for receiving the first locking element on its first end and a second transverse duct for receiving the second locking element on its second end,
wherein each of the locking elements comprises an anchoring section configured to provide anchoring of the locking element in pelvic bone, and a locking section that corresponds with one of the transverse ducts of the nail in such a manner that the locking element is lockable to the nail in an angular stable manner,
wherein the nail is configured to be fixed at its second end in a first pelvic bone and/or in the sacrum by the fixing device after having being passed through or into the sacrum,
wherein the nail is configured to be fixed against twisting and displacement at its first end relative to a second pelvic bone by the first locking element to provide for angular stable locking of the nail at both ends thereof in a pelvic bone and to maintain in an angular stable manner an external force exerted after fixation of the nail at its second end on the pelvic ring in the direction of the axial extension of the nail, and
a stabilization assembly configured to stabilize vertebral bodies, the stabilization assembly including a connection element configured to be arranged on an end of at least one of the locking elements, the connection element having a retaining body, and
a stabilization element configured to be passed through the retaining body and fixed with respect to the retaining body.

26. The implant system according to claim 25, wherein:
the connection element has a retaining body with a U-shaped recess and a screw configured to be screwed into a corresponding threading of the U-shaped recess, and the stabilization element is configured to be passed through the U-shaped recess of the retaining body and fixed with respect to the retaining body via a contact pressure from the screw.

* * * * *